(12) United States Patent
Yamka et al.

(10) Patent No.: US 9,888,709 B2
(45) Date of Patent: Feb. 13, 2018

(54) COMPOSITIONS AND METHODS FOR ENHANCING NEUROLOGICAL DEVELOPMENT

(75) Inventors: Ryan Michael Yamka, Topeka, KS (US); Kim Gene Friesen, Carthage, IN (US); Steven Curtis Zicker, Lawrence, KS (US)

(73) Assignee: Hlll's Pet Nutrition, Inc., Topeka, KS (US)

( * ) Notice: Subject to any disclaimer, the term of this patent is extended or adjusted under 35 U.S.C. 154(b) by 829 days.

(21) Appl. No.: 12/528,164

(22) PCT Filed: Feb. 22, 2008

(86) PCT No.: PCT/US2008/054786
§ 371 (c)(1),
(2), (4) Date: Aug. 21, 2009

(87) PCT Pub. No.: WO2008/118586
PCT Pub. Date: Oct. 2, 2008

(65) Prior Publication Data
US 2010/0093859 A1    Apr. 15, 2010

Related U.S. Application Data

(60) Provisional application No. 60/891,171, filed on Feb. 22, 2007.

(51) Int. Cl.
| | | |
|---|---|---|
| *A23K 50/40* | (2016.01) | |
| *A23K 20/174* | (2016.01) | |
| *A23K 20/105* | (2016.01) | |
| *A23K 20/142* | (2016.01) | |
| *A23K 20/158* | (2016.01) | |
| *A23K 20/20* | (2016.01) | |

(52) U.S. Cl.
CPC ............ *A23K 50/40* (2016.05); *A23K 20/105* (2016.05); *A23K 20/142* (2016.05); *A23K 20/158* (2016.05); *A23K 20/174* (2016.05); *A23K 20/30* (2016.05); *A23V 2002/00* (2013.01)

(58) Field of Classification Search
None
See application file for complete search history.

(56) References Cited

U.S. PATENT DOCUMENTS

| | | |
|---|---|---|
| 5,690,988 A | 11/1997 | Lin et al. |
| 5,851,573 A | 12/1998 | Lepine et al. |
| 6,071,544 A | 6/2000 | Sunvold |
| 6,426,100 B2 | 7/2002 | Watkins et al. |
| 6,582,752 B2 | 6/2003 | Kealy et al. |
| 6,517,877 B2 | 11/2003 | Gannon |
| 2002/0001640 A1 | 1/2002 | Watkins et al. |
| 2004/0028719 A1 | 2/2004 | Davenport et al. |
| 2005/0014698 A1 | 1/2005 | Friesen et al. |
| 2005/0084517 A1 | 4/2005 | Torney et al. |
| 2005/0266051 A1 | 12/2005 | Kelley et al. |
| 2006/0045909 A1 | 3/2006 | Friesen et al. |
| 2010/0093859 A1 | 4/2010 | Yamka et al. |

FOREIGN PATENT DOCUMENTS

| | | | |
|---|---|---|---|
| CA | 2679682 | 8/2008 | |
| CN | 1631207 | 6/2005 | |
| GB | 2367487 | 4/2002 | |
| JP | 01-157912 | 6/1989 | |
| JP | H4-166039 | 6/1992 | |
| JP | 2003-522788 | 7/2003 | |
| JP | 2005-533864 | 11/2005 | |
| WO | WO 00/44375 | 8/2000 | |
| WO | WO 00/72698 | 12/2000 | |
| WO | WO 04/012522 | 2/2004 | |
| WO | WO 04/080196 | 9/2004 | |
| WO | 2004095940 A | 11/2004 | |
| WO | WO 05/006877 | 1/2005 | |
| WO | WO 05/032271 | 4/2005 | |
| WO | 2006072084 A | 7/2006 | |
| WO | 2006074089 A | 7/2006 | |
| WO | WO 2006072084 A2 * | 7/2006 | |
| WO | WO 2006074089 A2 * | 7/2006 | ............... A01K 5/00 |
| WO | WO 07/041418 | 4/2007 | |
| WO | WO 08/018043 | 2/2008 | |

OTHER PUBLICATIONS

Jones, B., FAQ: Cat Reproduction, Sacramento Area Animal Coalition (Available on Jan. 10, 2010 at www.sacanimal.org/cat_reproduction_FAQ.pdf, complied by Barb Jones. Sources: Feldman EC, Nelso RW. Canine and Feline Endocrinology and Reproduction. Third ed. St. Louis, Missouri: Saunders 2004; Ptaszynka M., Compendium of animal reproduction. 7 ed.*

Jones, B., FAQ: Cat Reproduction, Sacramento Area Animal Coalition, Available on Jan. 10, 2010at http://www.sacanimal.org/cat_reproduction_FAQ.pdf, complied by Barb Jones. Sources: Feldman EC, Nelso RW. Canine and Feline Endocrinology and Reproduction. Third ed. St. Louis, Missouri: Saunders 2004; Ptaszynka M., Compendium of animal reproducti.*

WolframAlpha® computational knowledge engine (at http://www.wolframalpha.com/) conversions ("WolframAlpha® conversions").*

Jones, B., FAQ: Cat Reproduction, Sacramento Area Animal Coalition.*

Applicant's admitted prior art of commercial compositions A, A1 and B, specification- p. 10, ("Applicant's admitted prior art", of record).*

AAFCO Cat Food Nutrient Profiles, 2003 official publication, available at http://maxshouse.com/nutrition/aafco_cat_food_nutrient_profiles.htm ("AAFCO Cat Food").*

Hornstra et al., Essential fatty acids in pregnancy and early human development, European Journal of Obstetrics & Gynecology and Reproductive Biology, 61 (1995) 57-62 ("Hornstra").*

(Continued)

*Primary Examiner* — Svetlana M Ivanova

(57) ABSTRACT

Compositions and methods useful to enhance neurologic development of a growing animal are disclosed.

2 Claims, 1 Drawing Sheet

(56) References Cited

OTHER PUBLICATIONS

Email response from Sacramento Area Animal Coalition (SAAC) [mailto:contact@sacanimal.org] to Jonathan Fiencke (Senior Librarian; Jonathan.Fiencke@uspto.gov), Jun. 26, 2013.*

Hornstra et al., Essential fatty acids in pregnancy and early human development, 61 European Journal of Obstetrics & Gynecology and Reproductive Biology 57-62 (1995).*

Kreis, Development of the human brain: In vivo quantification of metabolite and water content with proton magnetic resonance spectroscopy, MRM 30:424-437 (1993).*

Robertson et al., Early increases in brain myo-inositol measured by proton magnetic resonance spectroscopy in term infants with neonatal encephalopathy, Pediatric Research, vol. 50, No. 6, 692-700, 2001.*

Waldron M K et al., "Role of Long-Chain Polyunsaturated N-3 Fatty Acids In The Development of the Nervous System of Dogs and Cats," Journal of the American Veterinary Medical Association (1998) pp. 619-622 213:5.

Pawlosky R J et al., "Retinal and Brain Accretion of Long-Chain Polyunsaturated Fatty Acids in Developing Felines: The Effects of Corn Oil-Based Maternaldiets," American Journal of Clinical Nutrition, (1997) pp. 465-472, 65:2 Bethesda, MD.

Frantz et al, 2007, "The Effect of Diet and Lysine: Calorie Ratio on Body Composition and Kidney Health in Geriatric Cats", International Journal of Applied Research in Veterinary Medicine, vol. 5(1), pp. 25-36.

Frantz et al., 2007, "Effect of Dietary Protein on Body Composition and Renal Function in Geriatric Dogs", International Journal of Applied Research in Veterinary Medicine, vol. 5(2), pp. 57-64.

ISR and Written Opinion for PCT/US08/054773 dated Jul. 21, 2008.
ISR and Written Opinion for PCT/US08/054786 dated Jul. 29, 2008.
ISR and Written Opinion for PCT/US08/054789 dated Jul. 21, 2008.
ISR and Written Opinion for PCT/US08/054796 dated Jul. 21, 2008.
ISR and Written Opinion for PCT/US08/054800 dated Jul. 24, 2008.

Milgram et al., 2002, "Landmark Discrimination Learning in the Dog. Effects of Age, An Antioxidants Fortified Food, and Cognitive Strategy", Neuroscience and Biobehavioral Reviews, 26, pp. 679-695.

Mutch et al, 2005, "An Integrative Metabolism Approach Identifies Stearoyl-Coa Desaturase as a Target for an Arachidonate-Enriched Diet", Faseb Journal 19:6, pp. 599-601.

Perez-Matute et al., 2007, "Eicosapentaenoic Acid Actions on Adiposity and Insulin Resistance in Control and High-Fat-Fed Rats: Role of Apoptosis, Adiponectin and Tumor Necrosis Factor-Alpha", British Journal of Nutrition, vol. 97, pp. 389-398.

Ringses et al., 2005, "Effects of Dietary Fat and Oxidized Cholestrol on Gene Expression in Rat Liver as Assessed by eDNA Expression Array Analysis", EUR J Nutr., 44, pp. 231-241.

Roudebush, 2001, "Flatulence: Causes and Management Options", Compendium, vol. 23(12), pp. 1075-1082.

Tapp et al., 2004, "Frontal Lobe Volume, Function, and Beta-Amyloid Pathology in a Caine model of Aging", Journal of Neuroscience 24(37):8205-13.

Tapp et al, 2006, "Application of an Automated Voxel-Based Morphometry Technique to Assess Regional Gray and White Matter Brain Atrophy in a Canine Model of Aging", Neuroimage 29:234-244.

Yamka et al., 2006, "Measurement of Arthritic and Bone Serum Metabolites in Arthritic, Non-Arthric, and Geriatric Cats Fed Wellness Food", International Journal of Applied Research in Veterinary Medicine, vol. 4(3), pp. 265-273.

\* cited by examiner

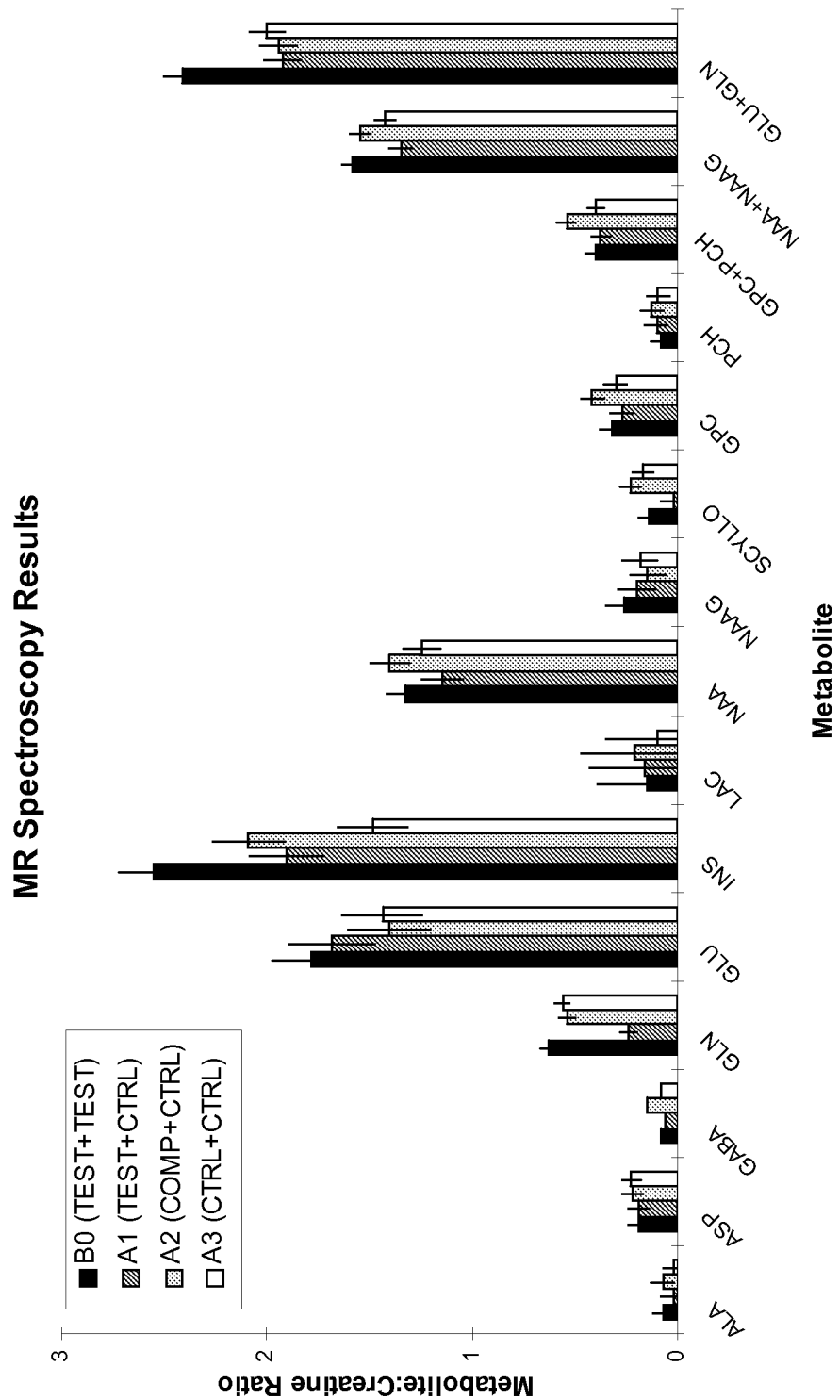

COMPOSITIONS AND METHODS FOR ENHANCING NEUROLOGICAL DEVELOPMENT

CROSS-REFERENCE TO RELATED APPLICATIONS

This application claims priority to U.S. Provisional Application No. 60/891,171, filed on Feb. 22, 2007 the contents of which are incorporated herein by reference.

FIELD OF THE INVENTION

The present invention relates to compositions and methods for enhancing the neurologic development of mammals.

BACKGROUND OF THE INVENTION

Commercially available pet foods, e.g., cat food, include compositions specially formulated to address many different nutritional needs. These include, for example, formulations designed for different breed types, sizes and body conditions. They also include formulations designed to address the nutritional needs of animals in the different stages of their life cycle. Despite the availability of such pet food formulations, however, there is a need to develop formulations and methods to address other aspects of an animal's health.

Nootropic agents are known in the art, and generally include drugs and compounds which improve cognative and neurologic development. Although nootropic agents have been used for many years, some of the agents are toxic or expensive to use in food products. Thus, it is desirable to develop compositions and methods which may aid in neurologic development of animals without increasing costs for manufacturing. Preferably, compositions containing materials which are readily available in the art may be utilized to improve neurologic development, however, specific formulations need to be developed before their advantages may be realized and appreciated.

SUMMARY OF THE INVENTION

In certain aspects, the present invention relates to compositions that are useful to enhance the neurologic development of an animal.

The present invention includes Composition 1.0, a pet food composition useful to neurologic development in an animal comprising:
  about 0.1% to about 0.7% DHA;
  about 2400 ppm to about 7500 ppm choline; and
  about 100 ppm to about 500 ppm carnitine.

In another aspect the invention relates to a pet food composition useful to enhance immune function in an animal comprising from about 200 to about 1200 IU/kg vitamin E, from about 50 to about 500 ppm vitamin C, from about 0.10% to about 0.60% EPA and from about 0.10% to about 0.50% DHA.

The present invention also includes the following compositions:
  1.1 Composition 1.0 comprising about 0.1% to about 0.50% DHA, e.g. about 0.1% to about 0.4%, e.g., about 0.2, about 0.3%, or about 0.4%;
  1.2 Composition 1.0 or 1.1 comprising about 200 to about 1200 IU/kg vitamin E, e.g., about 500 IU/kg, to about 1100 IU/kg, about 700, about 800, about 900, or about 1000 IU/kg;
  1.3 Any of the preceding compositions comprising about 50 to about 500 ppm vitamin C, e.g., about 100 to about 400 ppm Vitamin C, e.g. about 150, about 175, about 200, or about 225 ppm;
  1.4 Any of the preceding compositions comprising about 200, about 300, or about 400 ppm carnitine;
  1.5 Any of the preceding compositions comprising about 2.5 g/1000 kcal to about 7 g/1000 kcal lysine;
  1.6 Any of the preceding compositions comprising about 2500 ppm to about 7500 ppm choline, e.g., about 3000, about 4000, about 4500, about 4600, about 4625, about 4650, about 4700, about 5000, or about 6000 ppm;
  1.7 Any of the preceding compositions comprising about 0.1% to about 0.7% EPA. e.g. about 0.2%, about 0.3%, about 0.4%, or about 0.5%;
  1.8 Any of the preceding compositions comprising about 50 ppm to about 200 ppm manganese;
  1.9 Any of the preceding compositions comprising about 0.50% to about 1.6% methionine, e.g., about 0.8% to about 1.6% methionine, e.g., about 1.3 or about 1.4% methionine.
  1.10 Any of the preceding compositions further comprising:
    0 to about 90% by weight of carbohydrates;
    about 5% to about 70% by weight of protein;
    about 2% to about 50% by weight of fat;
    about 0.1% to about 20% by weight of total dietary fiber;
    0 to about 15%, preferably about 2% to about 8%, by weight of vitamins, minerals, and other nutrients, in varying percentages which support the nutritional needs of the animal.
  1.11 Composition 1.10 comprising about 5% to about 55%, by weight of carbohydrates;
  1.12 Composition 1.10 or 1.11 comprising about 20% to about 60%, by weight of protein. e.g., about 30-about 55%;
  1.13 Any one of compositions 1.10-1.12 comprising about 5% to about 40%, by weight of fat. e.g., at least about 8% or about 9% to about 40% fat;
  1.14 Any one of compositions 1.10-1.13 comprising about 1% to about 11%, by weight of total dietary fiber;
  1.15 Any of the preceding compositions comprising about 1000 to about 4000 ppm taurine;
  1.16 Any of the preceding compositions comprising about 0.5% to about 6% linoleic acid. e.g., about 2.5% to about 5%;
  1.17 Any of the preceding compositions comprising about 1% to about 3% total n-3 fatty acids, e.g. about 1.3%, about 1.4%, about 1.5%, or about 1.6%.
  1.18 Any of the preceding compositions comprising about 1% to about 6% total n-6 fatty acids, e.g., about 3% to about 5%, about 3.5%, or about 4%.

The compositions of the present invention may be a wet, dry, or semi-dry food.

The present invention includes Method 2.0, a method to enhance the neurologic development of a feline comprising administering to the feline any one of compositions 1.0-1.18.

The present invention also includes the following methods:
  2.1 Of method 2.0 wherein the feline is a kitten
  2.2 Of method 2.0 or 2.1 wherein the feline is born of a queen fed any one of compositions 1.0-1.15 during pregnancy.
  2.3 Of method 2.2 wherein the feline is in utero.

2.4 Of method 2.2 wherein the queen is fed any one of compositions 1.0-1.18 prior to pregnancy.

2.5 Of method 2.2 or 2.4 wherein the queen is fed any one of compositions 1.0-1.18 for a majority of the pregnancy duration.

2.6 Of any one of methods 2.2-2.5 wherein the queen is fed compositions consisting essentially of any one of compositions 1.0-1.18 prior to and during pregnancy.

2.7 Of any one of the preceding methods wherein the kitten is fed any one of compositions 1.0-1.18 prior to weaning, e.g., while still nursing.

2.8 Of any one of the preceding methods wherein the kitten is fed any one of compositions 1.0-1.18 post weaning.

2.9 Of method 2.8 wherein the kitten is fed food compositions consisting of any one of compositions 1.0-1.18.

2.10 Of any one of the preceding methods wherein an effective amount of the composition is administered to the animal.

2.11 Of any one of the preceding methods wherein the composition is administered to the animal for an effective amount of time.

It is also contemplated that, in addition to administering the compositions disclosed herein directly to a growing animal, e.g. to a growing puppy or kitten, the compositions may be administered to the dam of the animal while the animal is still in utero or while the animal is a nursling.

Other features and advantages of the present invention will be understood by reference to the detailed description of the examples that follow.

BRIEF DESCRIPTION OF THE DRAWINGS

FIG. 1 is magnetic resonance spectroscopy data relevant to Example 1.

DETAILED DESCRIPTION OF THE INVENTION

It is contemplated that the invention described herein is not limited to the particular methodology, protocols, and reagents described as these may vary. It is also to be understood that the terminology used herein is for the purpose of describing particular embodiments only, and is not intended to limit the scope of the present invention in any way.

Unless defined otherwise, all technical and scientific terms used herein have the same meanings as commonly understood by one of ordinary skill in the art to which this invention belongs. In addition, all references cited herein are hereby incorporated by reference in their entireties. In the event of a conflict in a definition in the present disclosure and that of a cited reference, the present disclosure controls.

As used herein and in the appended claims, the singular forms "a". "an", and "the" include plural reference unless the context clearly dictates otherwise.

The present invention relates to any animal, preferably a mammal, more preferably a companion animal. The term "companion animal" refers to any animal that lives in close association with humans and includes, but is not limited to, canines and felines of any breed. It is contemplated herein, however, that any animal whose diet may be controlled by humans may benefit from feeding the formulations disclosed herein. These animals may include, for example, domesticated farm animals (e.g., cattle, horses, swine, etc.) as well as undomesticated animals held in captivity. e.g., in zoological parks and the like. Preferably, the animal is a feline, either a kitten, or adult cat.

As used herein, "an amount effective to" or "an effective amount" to achieve a particular result, and like terms, refer to that amount of a compound, material or composition as described herein that may be effective to achieve a particularly desired biological result. As contemplated herein, such results include, for example, enhancement of neurologic development, bone and joint health, immune function and/or promotion of a healthy body composition of an animal, either while developing in utero and/or during its growth stage after birth, e.g. up to 6 months, 9 months, 12 months, or 15 months after birth. Such effective activity may be achieved, for example, by administration of compositions of the present invention to the dam of said animal while the animal is in utero or nursing, as well as by direct administration to the animal during its growth stage.

As used herein, the "enhancement" of a particular biological process or body condition in a growing animal such as described herein refers to an improvement in the biological process or body condition of a growing animal compared to a control animal. Improvement in such a process or condition may be determined by one of skill in the art.

As used herein, "enhancement of the development of a growing animal" or "enhanced growth" and like terms refer to an overall improvement in one or more biological processes and/or the body condition of a growing animal, including but not limited to, biological processes central to the growth and development of an organism, including, but not limited to, the biological processes described herein, e.g. bone and joint health, neurologic and immune system development and body weight gain (e.g., increase in lean muscle mass instead of adipose tissue).

The "growth" life stage of an animal refers to the period from birth or weaning (approximately 8 weeks of age) to about 1 year of age.

As used herein, the term "kitten" refers to an immature feline, typically between the ages of birth and 12 months.

"Essential amino acids" as used herein refers to those amino acids that cannot be synthesized de novo by an organism and thus must be supplied in the diet. It is understood by one of skill in the art that the essential amino acids vary from species to species, depending upon the organism's metabolism. For example, it is generally understood that the essential amino acids for dogs and cats (and humans), are phenylalanine, leucine, methionine, lysine, isoleucine, valine, threonine, tryptophan, histidine and arginine. In addition, taurine, while technically not an amino acid but a derivative of cysteine, is an essential for cats. A balanced diet can provide all the essential amino acids, however, there are certain essential amino acids that are more critical, as a diet deficient in one of them will limit the usefulness of the others, even if the other essential amino acids are present in sufficient quantities.

As understood by one of skill in the art, a "limiting amino acid" refers to an amino acid which if present in insufficient quantities in a diet, results in the limitation in usefulness of other essential amino acids, even if the other essential amino acids are present in otherwise large enough quantities. Lysine is the limiting essential amino acid in the compositions disclosed herein. Thus, the remaining essential amino acids are quantitatively formulated or "balanced" in relationship to the amount of lysine determined critical to affect the desired biological result. As used herein, "balanced amino acids" refers to the relationship of the essential amino acid lysine to energy to assure optimal animal growth and development.

"Essential nutrients" as used herein refers to nutrients required for normal body functioning that cannot be synthesized by the body. Categories of essential nutrient include vitamin dietary minerals, fatty acid, and amino acid. It is understood by one of skill in the art that the nutrients deemed essential varies from species to species, depending upon the organism's metabolism. For example, essential nutrients for dogs and cats include Vitamins A, D, E, K, B1, B6, B12, riboflavin, niacin, pantothenic acid, folic acid, calcium, phosphorous, magnesium, sodium, potassium, chlorine, iron, copper, zinc, manganese, selenium and iodine. Choline, generally regarded as a B complex vitamin, may be included among the semi-essential nutrients.

Carnitine, also known as L-carnitine, (levocarnitine) is a quaternary ammonium compound synthesized from the amino acids lysine and methionine and is responsible for the transport of fatty acids from the cytosol into the mitochondria.

Without being limited to any theories or particular modes of action, the present invention is based on the surprising discovery that the addition of certain ingredients to pet food compositions and administration of these compositions to animals can enhance the development of a growing animal. Data indicates that animals fed the compositions of the present invention (or those whose dams were fed the compositions during gestation and prior to weaning but continued throughout growth of their litters), demonstrate enhanced neurologic development. In one aspect, the invention relates to a method to enhance the neurologic development of a growing animal comprising administering to said animal a composition of the present invention. An enhancement in neurologic development may be indicated by better brain development, as measured by MRI spectroscopy, and/or by better cognitive and motor skill scores, compared to control animals. For instance, the state of neurologic development may be assayed by measuring the level of trainability in a growing animal to which is administered a composition of the present invention and comparing levels to a suitable control animal.

As contemplated herein, the compositions of the present invention comprise nutritionally complete and balanced animal feed compositions. Such compositions include, among other nutrients and ingredients, recommended healthful amounts of protein, carbohydrate and fat.

"Nutritionally complete and balanced animal feed compositions", as well as nutrients and ingredients suitable for animal feed compositions, and recommended amounts thereof, are familiar to one of skill in the art (see, for example, National Research Council, 2006 Nutritional Requirements for Dogs and Cats, National Academy Press, Washington D.C. or the Official Publication of the Association of American Feed Control Officials, Inc. Nutrient Requirements for Dogs and Cats 2006).

It is contemplated herein that the compositions disclosed herein may also comprise antioxidants, additives, stabilizers, thickeners, flavorants, palatability enhancers and colorants in amounts and combinations familiar to one of skill in the art. "Antioxidants" refers to a substance that is capable of reacting with or decreasing the production of free radicals and neutralizing them. Examples include, but are not limited to beta-carotene, selenium, coenzyme Q10 (ubiquinone), lutein, tocotrienols, soy isoflavones, S-adenosylmethionine, glutathione, taurine, N-acetylcysteine, vitamin E, vitamin D, vitamin C, flavanoids, anthocyanindins, and lipoic acid.

While foods of any consistency or moisture content are contemplated, preferably the compositions of the present invention may be, for example, a wet, semi-dry or dry animal food composition. "Wet" food refers to food which is sold in cans or foil bags and has a moisture content of about 70 to about a 90%. "Dry" food refers to compositions with about 5 to about 15% moisture content and is often manufactured in the form of small bits or kibbles. Semi-dry compositions refer to compositions having about 15% to about 70% moisture. Also contemplated herein are compositions of intermediate moisture consistency and those that may comprise components of various consistency as well as components that may include more than one consistency, for example, soft, chewy meat-like particles as well as kibble having an outer cereal component and an inner cream component as described in. e.g., U.S. Pat. No. 6,517,877.

The following examples further illustrate the present invention and are not intended to limit the invention. As used throughout, ranges are used as shorthand for describing each and every value that is within the range. Any value within the range can be selected as the terminus of the range. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

Example 1

Formulations to enhance the development of growing animal are disclosed here-in-below. These compositions are developed taking into account the "ideal protein concept" (Baker and Czarnecki-Maulden. 1991 Annu. Rev. Nutr. 11:239-63).

Foods are developed for the "growth" life stage. These foods include formulations for canine growth and feline growth. The minimum nutrient recommendations for these foods, as well as the targeted values for a prototype food, are listed below in Table 1.

TABLE 1

Key Nutrients for Kitten Formula

| Nutrient | Target | Minimum | Maximum |
| --- | --- | --- | --- |
| Protein, % | 45.5 | 30 | 55 |
| Methionine, % | 1.4 | 0.8 | 1.6 |
| Manganese, ppm | 90 | 50 | 200 |
| DHA, % | 0.21 | 0.1 | 0.5 |
| EPA, % | 0.31 | 0.1 | 0.70 |
| Choline, ppm | 4880 | 2500 | 7500 |
| Taurine, ppm | 2380 | 1000 | 4000 |
| Linoleic acid, % | 3.8 | 2.5 | 6.0 |
| Total n-3 fatty acids, % | 1.35 | 1.0 | 3.0 |
| Vitamin E, IU/kg | 900 | 200 | 1200 |
| Vitamin C, ppm | 90 | 50 | 500 |
| Lysine, g/1000 kcal | 4 | 2.5 | 7 |

Example 2

Four foods are used for the study, experimental Formulation X, Commercial A, Commercial A1, and Commercial B. The composition of the foods is presented in Table 2, Commercial A, A1, and B foods are available from commercial sources. Commercial A and A1 are the same brand of food, but produced in different lots.

TABLE 2

Analyzed nutrients of foods fed to queens and kittens

| Nutrient, | Formula X | Commercial A | Commercial A1 | Commercial B |
|---|---|---|---|---|
| Crude Protein, % | 41.63 | 41.2 | 36.09 | 35.47 |
| Fat, % | 23.15 | 14.47 | 12.43 | 22.94 |
| Ca, % | 1.23 | 1.12 | 1.50 | 1.06 |
| P, % | 1.11 | 1.11 | 1.19 | 0.96 |
| DHA, % | 0.22 | 0.06 | 0.04 | <0.01 |
| EPA, % | 0.32 | 0.06 | 0.04 | <0.01 |
| Linoleic Acid, % | 3.79 | 1.59 | 1.96 | 1.37 |
| Total n-3 fatty acids, % | 1.47 | 0.34 | 0.25 | 0.53 |
| Total n-6 fatty acids, % | 3.86 | 1.88 | 1.91 | 1.44 |
| Taurine, % | 0.24 | 0.17 | 0.23 | 0.20 |
| Methionine, % | 1.3 | 0.76 | 0.62 | 0.99 |
| Cystine, % | 0.49 | 0.51 | 0.44 | 0.35 |
| Manganese, ppm | 78 | 63 | 77 | 56 |
| Vitamin E, IU/kg | 914 | 35 | 76 | 138 |
| Vitamin C, ppm | 183 | — | — | — |
| Choline, ppm | 4624 | 3010 | 2807 | 3331 |

19 queens are fed Formulation X or Commercial A for at least 2 weeks prior to conception. Queens are maintained in group lodging until they are confirmed pregnant via palpation, and are then moved to maternity lodging. 48 kittens are produced from queens fed Commercial A, and 16 kittens are produced from queens fed Formulation X. Following birth of kittens, the kittens from queens are kept on same foods until the kittens are weaned.

Following weaning, the 48 kittens produced from queens fed Commercial A were divided as follows: 16 kittens are fed Commercial A1 (Group A3 in FIG. 1); 16 kittens are fed Commercial B (Group A2 in FIG. 1); and 16 kittens are fed Formulation X (Group A1 in FIG. 1). Following weaning, the 16 kittens produced from the queens fed Formulation X are maintained on Formulation X (Group B0 in FIG. 1).

Brain imaging studies are performed when kittens are 7 months old to assess neurologic growth and development. Brain metabolites are assessed with magnetic resonance imaging using single-voxel spectroscopy. Each subject is pre-medicated with a single bolus injection of atropine and acepromazine administered intramuscularly or subcutaneously. Anesthesia is induced using an appropriate injectable anesthetic and is maintained using an isoflurane-oxygen mixture.

Magnetic imaging procedures are conducted using a GE-LX 1.5T MRI scanner. LX hardware configuration. 9.0 software level. The subject is placed into the magnet in a prone position with the head inside a quadrature transmit-receive knee coil for imaging. The specific parameters for each acquisition type are: APRESS, or point-resolved spectroscopy (Probe-P) with pulse sequence (TR=1500 msec; TE=102 msec; single voxel placed in centre of brain=8 ml; NEX=256) is performed for each kitten. Total acquisition time is approximately 7 minutes. The concentrations of metabolites in Table 3 are determined using the LC Model fitting procedure.

TABLE 3

Spectroscopy metabolites and their abbreviations

| Abbreviation | Metabolite |
|---|---|
| Ala | L-alanine |
| Asp | Aspartate |
| Cr | Creatine |
| GABA | gamma-aminobutyric acid |
| Gln | Glutamine |
| Glu | Glutamate |
| Ins | myo-inositol |
| Lac | L-lactate |
| NAA | N-acetylaspartate |
| NAAG | N-acetlaspartylglutamate |
| Scyllo | scyllo-inositol |
| GPC | glycerophosphocholine |
| PCh | phosphocholine |

A separate analysis of the ratios of each metabolite concentration to the creatine level for the same group is conducted, with a square root transformation to reduce heterogeneity of variance and non-normality. Results are presented in FIG. 1 and Table 4.

TABLE 4

Summary of MR spectroscopy ANOVA results - metabolite:creatine ratios

| Variable | Effect | Ratio |
|---|---|---|
| Scyllo | Food | 3.21 |
| INS | Food | 3.54 |
| NAAG | Sex | 3.99 |
| NAA + NAAG | Sex | 3.71 |
| NAAG | Food + Sex | 2.87 |
| NAA + NAAG | Food + Sex | 4.00 |

What we claim:
1. A composition comprising:
   about 0.1% to about 0.5% DHA;
   about 2500 ppm to about 7500 ppm choline;
   about 200 IU/kg to about 1200 IU/kg vitamin E;
   about 50 to about 500 ppm vitamin C;
   about 2.5 g/1000 kcal to about 7 g/1000 kcal lysine;
   about 0.1% to about 0.6% EPA;
   about 0.5% to about 1.6% methionine;
   about 30% to about 55% protein;
   about 1000 to about 4000 ppm taurine;
   about 2.5% to about 6.0% linoleic acid; and
   about 1% to about 3.0% omega-3 fatty acids.
2. The composition of claim 1, further comprising: 0 to about 90% by weight of carbohydrates; about 2% to about 50% by weight of fat; about 0.1% to about 20% by weight of total dietary fiber; and 0 to about 15% by weight of vitamins, minerals, and other nutrients.

* * * * *